United States Patent
Heinrich et al.

(10) Patent No.: US 10,687,712 B2
(45) Date of Patent: Jun. 23, 2020

(54) AUTOMATIC CONTINUOUS PATIENT MOVEMENT MONITORING

(71) Applicant: KONINKLIJKE PHILIPS N.V., Eindhoven (NL)

(72) Inventors: Adrienne Heinrich, Den Bosch (NL); Ahmet Ekin, Eindhoven (NL); Yingrong Xie, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 14/905,162

(22) PCT Filed: Jul. 9, 2014

(86) PCT No.: PCT/IB2014/062959
§ 371 (c)(1),
(2) Date: Jan. 14, 2016

(87) PCT Pub. No.: WO2015/011591
PCT Pub. Date: Jan. 29, 2015

(65) Prior Publication Data
US 2016/0150966 A1    Jun. 2, 2016

Related U.S. Application Data

(60) Provisional application No. 61/856,837, filed on Jul. 22, 2013.

(51) Int. Cl.
*A61B 5/00* (2006.01)
*G06T 7/215* (2017.01)
*A61B 5/11* (2006.01)

(52) U.S. Cl.
CPC .......... *A61B 5/0077* (2013.01); *A61B 5/0064* (2013.01); *A61B 5/1114* (2013.01);
(Continued)

(58) Field of Classification Search
CPC ... A61B 5/0064; A61B 5/0077; A61B 5/1114; A61B 5/1128; G06T 7/215
See application file for complete search history.

(56) References Cited

U.S. PATENT DOCUMENTS 7,545,279 B2    6/2009  Sato
9,245,338 B2 *  1/2016  Mestha .............. G06K 9/00362
(Continued)

FOREIGN PATENT DOCUMENTS

EP    0919184    6/1999
EP    1645840    4/2006
(Continued)

OTHER PUBLICATIONS

M. Alnowami et al, "A quantitative assessment of using the Kinect for Xbox360 for respiratory surface motion tracking", Proceedings of SPIE, vol. 8316, Feb. 13, 2012 (Feb. 13, 2012), p. 83161T, XP055148668.
(Continued)

*Primary Examiner* — Tammie K Marlen

(57) ABSTRACT

A monitoring system (10) includes at least one video camera (14), a motion unit (40), and a segmentation unit (42). The at least one video camera (14) is configured to continuously receive video of a subject in normal and darkened room conditions. The motion unit (40) identifies clusters of motion of the subject based on respiratory and body part motion in the received video of the subject. The segmentation unit (42) segments body parts of the subject based on the identified clusters of subject motion.

13 Claims, 7 Drawing Sheets

(52) U.S. Cl.
CPC .......... *A61B 5/1128* (2013.01); *A61B 5/4806* (2013.01); *A61B 5/6824* (2013.01); *G06T 7/215* (2017.01); *G06T 2207/10016* (2013.01); *G06T 2207/30196* (2013.01)

(56) References Cited

U.S. PATENT DOCUMENTS

| | | | |
|---|---|---|---|
| 9,412,161 B2* | 8/2016 | Varaklis | A61B 5/1124 |
| 2009/0189771 A1 | 7/2009 | Liu | |
| 2010/0063419 A1 | 3/2010 | Mostafavi et al. | |
| 2010/0124363 A1 | 5/2010 | Ek | |
| 2011/0144517 A1* | 6/2011 | Cervantes | A61B 5/08 |
| | | | 600/538 |
| 2012/0075464 A1 | 3/2012 | Derenne et al. | |
| 2012/0201468 A1 | 8/2012 | Oami et al. | |
| 2013/0324875 A1 | 12/2013 | Mestha | |
| 2014/0275832 A1 | 9/2014 | Muehlsteff | |
| 2014/0371599 A1* | 12/2014 | Wu | A61B 5/0077 |
| | | | 600/476 |

FOREIGN PATENT DOCUMENTS

| | | |
|---|---|---|
| JP | 11225997 | 8/1999 |
| WO | 2012/164453 | 12/2012 |
| WO | 2013050912 | 4/2013 |
| WO | 2013052123 | 4/2013 |

OTHER PUBLICATIONS

Wei Zhang et al, "Real-time clothes comparison based on multi-view vision", Distributed Smart Cameras, 2008. ICDSC 2008. Second ACM/IEEE International Conference on, IEEE, Piscataway, NJ, USA, Sep. 7, 2008 (Sep. 7, 2008), pp. 1-10,XP031329260.

Jamie Shotton et al, "Real-time human pose recognition in parts from single depth images", Computer Vision and Pattern Recognition (CVPR), 2011 IEEE Conference on, IEEE, Jun. 20, 2011 (Jun. 20, 2011), pp. 1297-1304,XP032037818.

Junyi Xia et al, "A real-time respiratory motion monitoring system using: Proof of concept", Medical Physics, AIP, Melville, NY, US, vol. 39, No. 5, May 1, 2012(May 1, 2012), pp. 2682-2685, XP012161024.

Christian Schaller, et al., "Time-of-flight sensor for respiratory motion gating", Medical Physics, vol. 35, No. 7, Jun. 13, 2008.

* cited by examiner

AUTOMATIC CONTINUOUS PATIENT MOVEMENT MONITORING

CROSS REFERENCE TO RELATED APPLICATIONS

This application is the U.S. National Phase application under 35 U.S.C. §371 of International Application No. PCT/IB2014/062959, filed Jul. 9, 2014, published as WO 2015/011591 on Jan. 29, 2015, which claims the benefit of U.S. Provisional Patent Application No. 61/856,837 filed Jul. 22, 2013. These applications are hereby incorporated by reference herein.

BACKGROUND

The following relates generally to medical imaging and patient monitoring. It finds particular application in conjunction with continuous patient movement monitoring of potential delirium patients, and will be described with particular reference thereto. However, it will be understood that it also finds application in other usage scenarios and is not necessarily limited to the aforementioned application.

Movement can provide information about a patient's state and wellbeing. For example, delirium is a common acute disorder affecting many adults in hospitals and can be identified by specific movements such as grabbing in the air, pinching skin, or repetitive and continuous head, arm or leg movements. Other patient movements can indicate a change in patient status and/or emergency such as falling out of a bed, getting out of bed, pulling at or on medical equipment, etc. Patient movements are typically analyzed by sporadic observation of healthcare practitioners which may miss movements and corresponding changes in patient conditions. For example, the sporadic observation by healthcare practitioners introduces a non-negligible lag in the detection of critical problems such as delirium.

A previous approach to patient movement monitoring included the use of an on-body wrist sensor or accelerometer. The presence of the on-body wrist sensor or other body worn sensor can be disturbing to a patient. The wrist sensor does not capture movements performed by other body parts. The wrist sensor does not allow identification of higher-level interpreted movements such as "pinching skin", "grabbing air", pulling on medical equipment, falling out of bed, getting out of bed, etc.

Several factors complicate an approach based on continuous analysis of video of the patient. One factor is the recognition of the patient and the identification of the patient's body parts separate from the many possible environments. The recognition of the patient and the identification of body parts can be further complicated by the presence of a covering such as a blanket, which may obscure direct observation of body parts. Another factor may be the intermittent presence of visitors or healthcare practitioners which may obscure or overlap portions of the patient's anatomy visible to video. Another complicating factor is changes in lighting.

The following discloses a new and improved automatic continuous patient movement monitoring which addresses the above referenced issues, and others.

BRIEF SUMMARY

In accordance with one aspect, a monitoring system includes at least one video camera, a motion unit, and a segmentation unit. The at least one video camera is configured to continuously receive video of a subject in normal and darkened room conditions. The motion unit identifies clusters of motion of the subject based on the received video of the subject. The segmentation unit segments body parts of the subject based on the identified clusters of subject motion.

In accordance with another aspect, a method of monitoring movement of a subject includes continuously receiving video of the subject in normal and darkened room conditions. Clusters of motion of the subject are identified based on constructed absolute difference images between a current image and a plurality of reference images in a temporal neighborhood of the received video of the subject. Body parts of the subject are segmented based on the identified clusters of subject motion.

In accordance with another aspect, a patient monitoring system includes a plurality of thermal or near infrared video cameras which include at least one camera configured to continuously receive video of one patient, and at least one configured processor. The at least one processor is configured for the at least one camera to compute a difference signal based on the absolute differences between a current image and a plurality of reference images in a temporal neighborhood from the received video of the subject, and identify a cluster of respiratory motion of the subject based on the difference signal. The at least one processor is further configured to segment an upper body of the body parts based on the identified cluster of respiratory motion of the subject and identify at least one cluster of non-respiratory motion. The at least one processor is yet further configured to segment at least a head and a trunk of the body parts based on the identified at least one cluster of non-respiratory motion and body proportions, and classify subject motion based on a frequency and a change in distance of identified motion and the segmented body parts.

One advantage resides in continuous monitoring of patient movement.

Another advantage resides in the monitoring a plurality of patient body parts for movement.

Another advantage resides in movement identification with or without a covering of the patient's body parts.

Another advantage resides in the monitoring of patients without physically attaching sensors to the patient body.

Another advantage resides in the monitoring and separating of patient movements from visitors, healthcare practitioners, and/or healthcare equipment.

Another advantage includes the identification and segmentation of patient body parts and the identification of higher-level interpreted movements.

Still further advantages will be appreciated to those of ordinary skill in the art upon reading and understanding the following detailed description.

The invention may take form in various components and arrangements of components, and in various steps and arrangement of steps. The drawings are only for purposes of illustrating the preferred embodiments and are not to be construed as limiting the invention.

DETAILED DESCRIPTION

Figure 1:
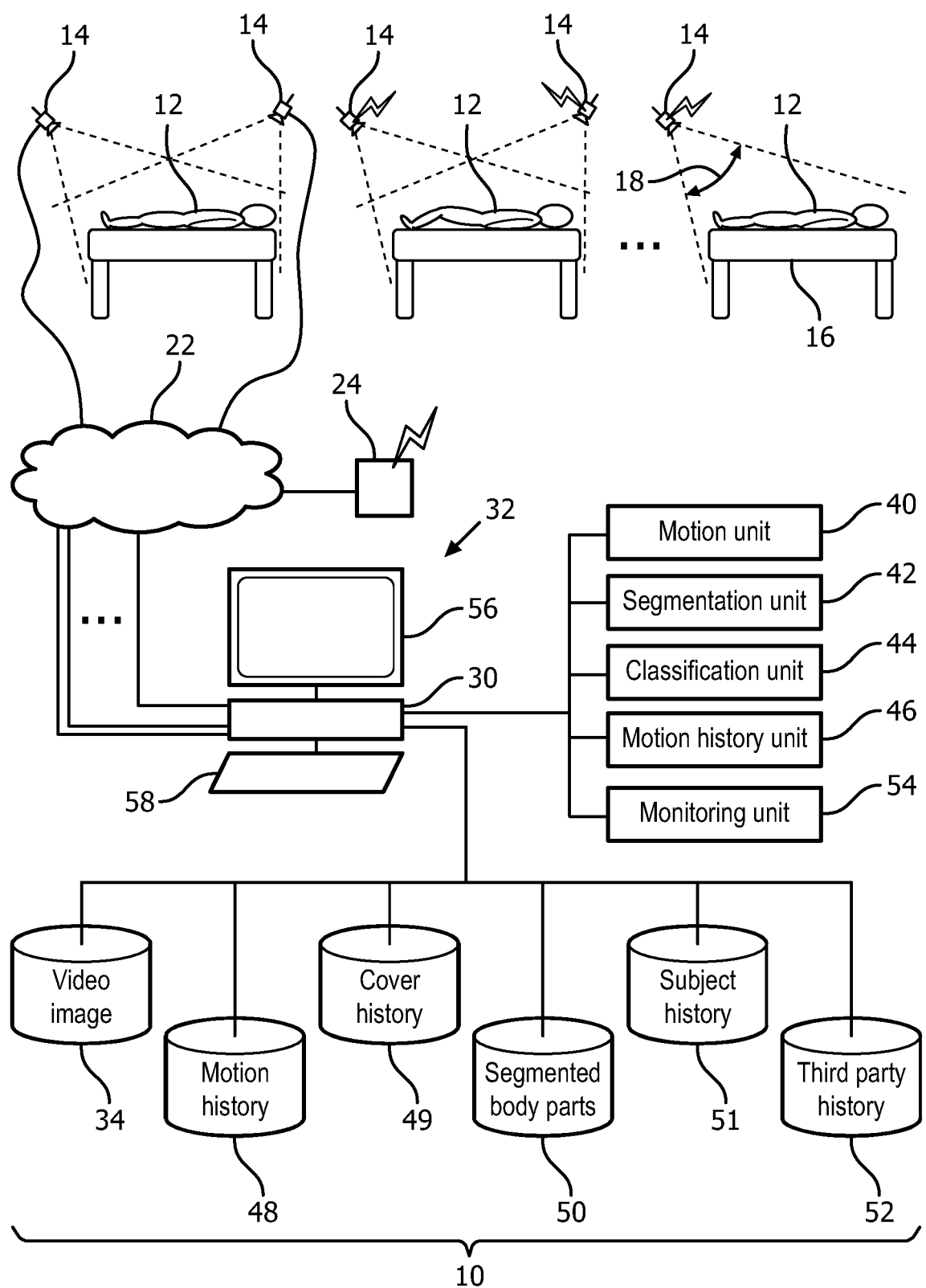
FIG. 1 schematically illustrates an embodiment of an automatic continuous patient movement monitoring system.

With reference to FIG. 1, an embodiment of an automatic continuous patient movement monitoring system 10 is schematically illustrated. The system monitors individual subjects 12 with at least one camera 14 such as a video camera, a thermal camera, a near infrared camera, e.g. nightvision, or a combination thereof. The camera continuously stream images of the subject such as hospital patients in normal light room conditions and darkened room conditions such as during the night. The subject is typically at rest on a bed 16 and the camera is positioned with a field of view 18 that includes the subject and bed, but can extend to the room 20. The camera 14 can be configured to operate wired or wireless, and can include a network 22 and/or a video distribution/collection device 24 for transmission of the streaming video. A single camera images a subject which includes 2-dimensional (2-D) measurements or two or more cameras can image a subject for 3-dimensional (3-D) measurements.

The video stream from each camera is streamed to one or more processors 30 such as the processor of a computer or workstation 32. The video images can be stored in a video image data store 34. The data store can include random access memory (RAM) or non-transitory computer readable media such as disk, solid state disk, server storage, etc. The data store can include file structure, database structure, and the like. The processing can include separate monitoring, e.g. dedicated workstation, or combined monitoring, e.g. configured server. The workstation can include other functions such as central monitoring of vital signs for one or more subjects. The workstation can be part of or connect to a central monitoring system with alerts or alarms.

The system includes a motion unit 40 which receives the video images or streamed video of the subject. The motion unit identifies clusters of motion of the subject based on constructed absolute difference images. The absolute difference image is constructed from a current image and any reference image in a temporal neighborhood.

A segmentation unit 42 segments body parts of the subject based on the identified clusters of motion and body proportions. The segmentation unit operates progressively to segment body parts as additional motion is present in the received video and clustered by the motion unit. The segmentation operates to first locate the subject in the motion clusters by identifying respiratory motion and segmenting the cluster as the trunk/chest area. As additional non-respiratory motion is present in the motion clusters, the segmentation builds a body mask to segment the body parts and associate the motion cluster with each body part. The segmentation unit identifies the body axis by fitting a line through clusters representing the segmented body parts such as the head, chest, and legs.

A classification unit 44 classifies subject motion based on a frequency and measures of motion of the clusters and segmented body parts such as angle, speed, location, distance, acceleration, and the like. For example, a movement of the trunk/chest area of the subject from the bed to a floor with the body axis remaining parallel to the bed/floor is indicative of a patient falling out of bed. In another example, a movement of the trunk/chest area of the subject from the bed to an elevated level and a change in body axis from parallel to the floor to perpendicular to the floor is indicative of a patient getting out of bed. The classification unit can interpret the repetitiveness of body part motions and motion measures of higher-level motions. For example, higher-level motions such as pinching skin, grabbing at the air indicative of delirium can be classified. The classification unit can also de-identify recorded video, e.g. insert into the video a covering over a patient's face and other parts of the body which may identify the patient.

A motion history unit 46 records each motion cluster in a motion history data store 48. The motion history unit records the presence and location or absence of a covering in a cover data store 49. The motion history unit records the segmented body parts in a segmented body parts data store 50. The motion history unit identifies and records clusters associated with the subject. The motion history unit stores the subject clusters in a subject history data store 51. The motion history unit can identify and record motion clusters associated with a third party. The motion history unit stores the third party clusters in a third party history data store 52. The motion history data store 48, the cover data store 49, the segmented body parts data store 50, the subject history data store 51, and the third party history data store 52 can be combined in a single data store or a combination of data stores.

A monitoring unit 54 receives and configures for display the classified motion and corresponding history portion of the video image, e.g. time segment of video. The monitoring unit can display an alarm or alert on a display device 56 such as the display device of the workstation 32 or communicate the alarm or alert to a central monitoring station. The monitoring unit can also configure for display a current video image. The configured display can include a composite display of different camera angles and/or multiple subjects. The configured display can include display of historical video images by classified motion, alarm, alert and/or time.

The workstation 32 includes the electronic processor or electronic processing device 30, the display device 56 which displays the video images, classifications, alerts, alarms, menus, panels, and user controls, and at least one input device 58 which inputs the healthcare practitioner selections. The workstation 20 can be a desktop computer, a laptop, a tablet, a mobile computing device, a smartphone, and the like. The input device can be a keyboard, a mouse, a microphone, and the like. The display device can include a computer monitor, a television screen, a touch screen, tactile electronic display, Cathode ray tube (CRT), Storage tube, Flat panel display, Light-emitting diode (LED) displays, Electroluminescent display (ELD), Plasma display panels (PDP), Liquid crystal display (LCD), Organic light-emitting diode displays (OLED), a projector, Head-mounted display, and the like.

The various units 40, 42, 44, 46, and 54 are suitably embodied by an electronic data processing device, such as the electronic processor or electronic processing device 30 of the workstation 32, or by a network-based server computer operatively connected with the workstation 32 by the network 22, or by individual electronic units, ASICs, programmable gate arrays, or so forth. Moreover, the disclosed clustering, segmentation, classification and monitoring techniques are suitably implemented using a non-transitory storage medium storing instructions (e.g., software) readable by an electronic data processing device and executable by the electronic data processing device to perform the disclosed techniques.

Figure 2:
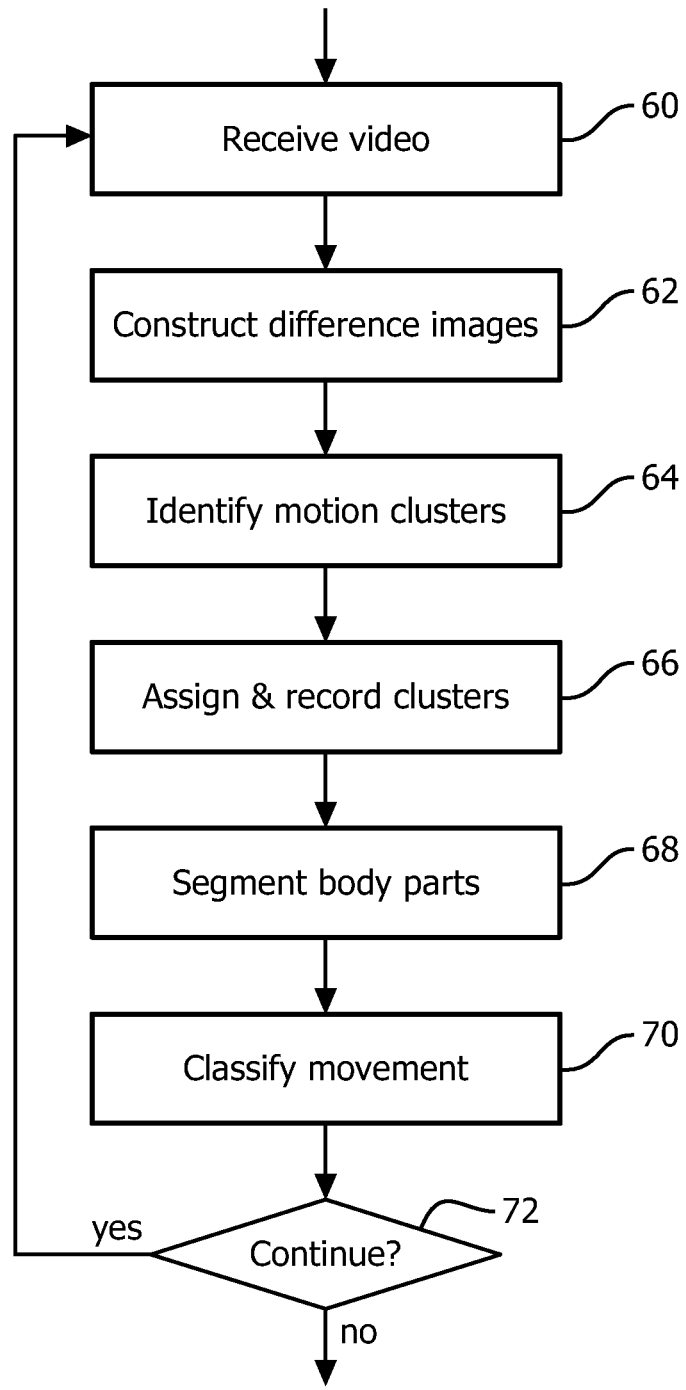
FIG. 2 flowcharts one embodiment of a method of automatic continuous patient movement monitoring.

With reference to FIG. 2 one embodiment of a method of automatic continuous patient movement monitoring is flowcharted. In a step 60, video images of the subject in normal and darkened room conditions are continuously received. The images can be filtered. Intensity can be normalized to compensate for dark scenes. Areas of subtle movement due to breathing are identified in a step 62 such as constructing absolute difference images. The difference images are the difference between a current image and a reference or preceding image taken in a temporal neighborhood. The difference image can be based on intensity and/or other image values such as color, contrast, etc. The areas or regions of difference form clusters of pixels in 2-D or voxels in 3-D. Other techniques such as correlation of spatial features, texture analysis, and the like which provide measures of movement can used. The techniques can use whole images or regions of interest.

The clusters of subject motion are identified based on the difference images in a step 64. For example, a cluster of respiratory motion is identified based on a size of the cluster and the periodicity of motion over time. Respiration motion is identified when large body part motion of the chest is absent, e.g. no turning of the body. Inability to measure respiratory motion when large part motion of the chest is present can be determined. Non-respiratory motion clusters are identified. Each motion cluster can include attributes of a size, a shape, a direction, a distance, physical location relative to chest or other identified cluster, and/or a velocity. The attributes can be relative to the respiratory cluster and be relative to the body proportions of the subject. The identified clusters can include the presence or absence of a covering of the subject body part.

In a step 66, the clusters are assigned and recorded. The assignment can include the subject or one or more third parties. For example, a cluster in close proximity to the chest and of a predetermined size and minimal distance change from image to image can be representative of a head of the subject and the assignment is the subject. In another example, a cluster which appears from the outer edge of the video image or a predetermined distance from the respiratory cluster can be representative of a third party and the assignment is a third party. Recording the cluster position and movement provides additional information for each additional movement of the cluster.

In a step 68, the body parts of the subject are segmented based on the identified clusters of subject motion. Initially, a cluster of respiratory motion is identified which is segmented into a chest body part. As additional clusters of non-respiratory motion are identified, additional body parts are segmented. The segmented body part correspondence to an identified cluster is refined and tracked. Body parts are segmented based on body proportions, proximity and orientation to the segmented trunk/chest.

The movement of the motion clusters is classified in a step 70. For example, the movement of the various clusters corresponding to specific body parts of the subject may suggest standing, falling, walking, sitting up, eating, etc. The motion attributable to a third party can be used to document treatment or clinician monitoring times and in some cases the administration of treatment. The movement analysis separates the motion clusters assigned to the subject and the motion clusters assigned to any third party. Classifying movement can include providing alerts and/or alarms based on the classification.

The process of receiving video, identifying, assigning, segmenting and classifying is repeated in a step 72. The process iteratively builds and refines segmentation of the body parts, tracks movement of the subject, and any third parties.

Figure 3:
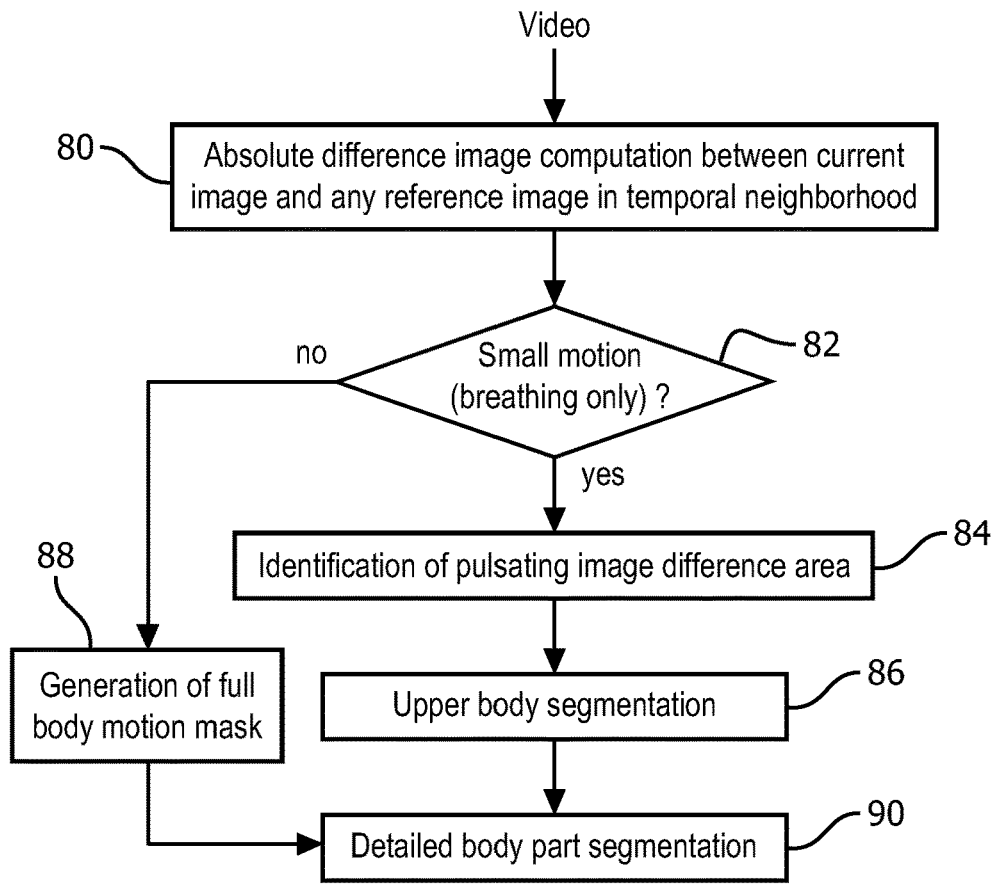
FIG. 3 flowcharts one embodiment of a method of localizing the subject in a video feed and performing a coarse body part segmentation.

With reference to FIG. 3 one embodiment of a method of identifying the subject in a video feed based on a difference signal is flowcharted. In a step 80, absolute difference images are computed between the current image and the reference image. The difference images include adjustments for camera angle, bed back rest tilt, different patient lying positions, and the presence or absence of a covering of body parts. In a decision step 82, the presence of small repetitive motion, e.g. the patient is breathing and lying still is determined based on the difference images. If the motion cluster is small, then in a step 84, a difference signal is computed based on the difference images to temporally and spatially to identify a cluster which pulsates. The pulsating motion cluster represents respiratory motion. In a step 86, the chest/upper arm area or trunk is segmented. Segmentation can include edge/gradient analysis, luminance value analysis, and object detection.

If the motion cluster is not small, e.g. large body movement, then a full body mask or silhouette is generated in a step 88. Large body movement such as turning in bed includes stepwise movement. For example, first is arm movement, next is leg movement, then head movement, and then chest movement. In a step 90, body parts are further segmented based on the previously identified segmented chest and the generated full body mask. Segmentation can include body proportions in the generation of the full body mask or separately to further segment body parts.

Figure 4:
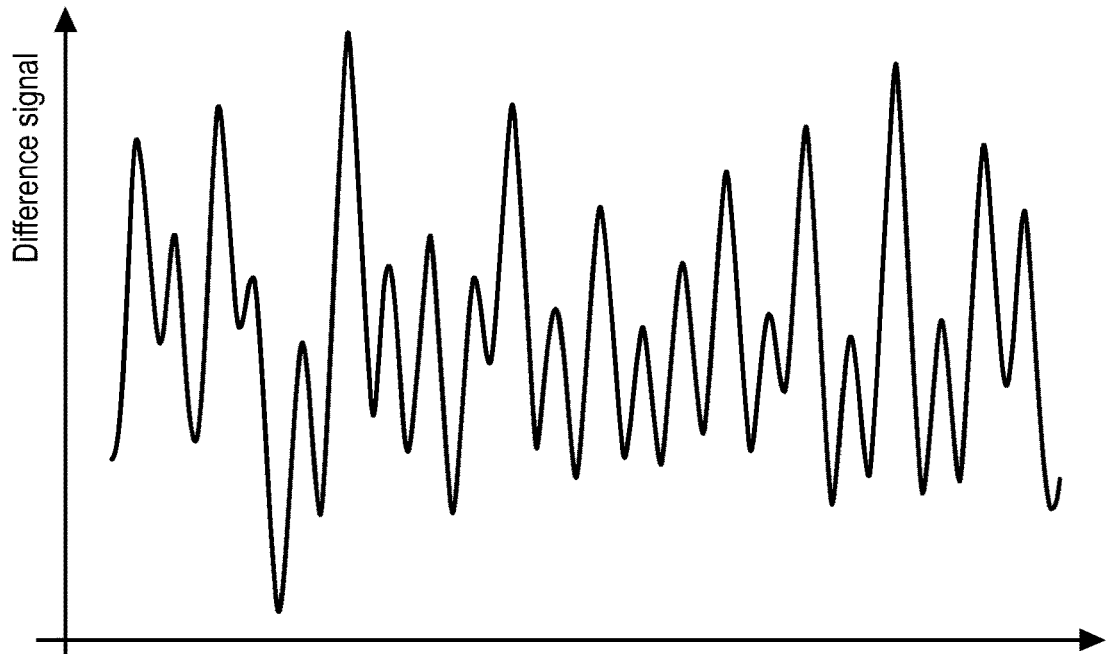
FIG. 4 illustrates an exemplary difference signal.

In FIG. 4 an exemplary difference signal is illustrated. As described in reference to FIG. 3, the difference signal identifies movement due to respiration. The difference signal is based on a selected arbitrary reference frame. The difference signal is computed by subtracting the selected reference frame from a video image segment and then summing the difference image, e.g. summing all difference pixels. The illustrated difference signal is plotted with the difference signal value on the y-axis and time on the x-axis. The signal peaks correspond to respiratory cycles, e.g. peak to peak corresponds to one respiratory cycle. The periodicity of the signal clearly indicates movement indicative of respiration. The difference signal can be used to identify the motion cluster which represents the chest area separate from other body part movement.

Figure 5:
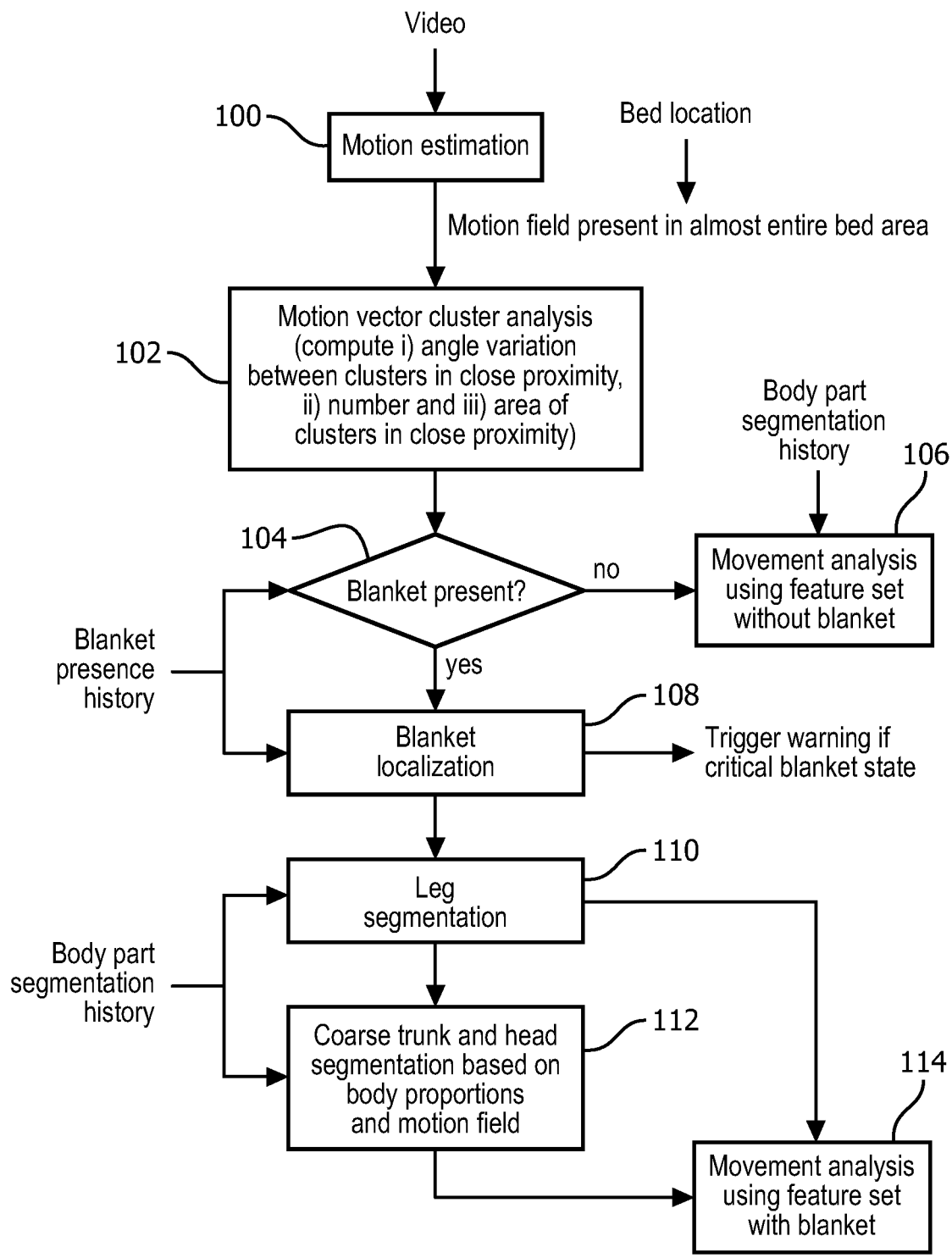
FIG. 5 flowcharts one embodiment of a method of movement analysis which includes accommodating a covering over the subject.

With reference to FIG. 5, one embodiment of a method of movement analysis which includes accommodating a covering over the subject is flowcharted. In a step 100 motion is estimated using two consecutive images which return motion vectors with speed and angle. In a step 102, attributes of the motion clusters are computed such as angle variation between neighboring clusters, the number of clusters, and the size of the clusters. The step can include object identification such as the bed and determination of the location of the clusters relative to identified objects.

The presence or absence of a covering is determined in a step 104 based on attributes of the motion clusters. For example, large, more diffuse clusters in close proximity are present with leg movement under a blanket compared to leg movement without any covering.

A feature set for non-covered movement is selected in a step 106 and the movement classified. The classification includes the segmented body parts 50 history previously segmented. The step can include further refinement of the segmented body parts. For example, a single non-repetitive arm movement not covered is classified as normal sleeping movement. The arm can be further segmented, e.g. upper arm, forearm, hand, etc. and the position recorded in the body parts segmentation.

In a step 108, the location of the covering is estimated. The extent of the motion clusters represents the location of the covering along with edge detection and/or textile recognition. For example, a blanket can be used with a known texture and/or color easily identified by automated means. The step can include refinement and/or modification of stored information in the cover data store 49. The step can include comparison with the segmented body parts. For example, a location of the cover over the segmented head of the subject can trigger an alert to a healthcare practitioner.

In a step 110, body parts such as legs are segmented which can include attributes based on a covering. The segmented body parts can be additional or a refinement of previously recorded body parts such as store in the segmented body parts data store 50. Cover present attributes can include motion vectors which propagate along the covering, and greater generalized movement. Body part segmentation can be further modified in a step 112 based on the body part segmentation history, and a body axis orientation.

A feature set for covered movement is selected and the movement classified in a step 114. For example, leg movement under a blanket selects a covered feature set which establishes attributes of motion clusters associated with leg movement. The selected feature set attributes are compared with the attributes of motions clusters such as size, distance, direction, speed, orientation, frequency, etc. and association with segmented body parts to classify the movement. For example, a repetitive side to side motion relative to a body axis can suggest delirium in combination with repetitive side to side of the head in contrast to a single movement parallel to the axis of the body by one leg which suggests a normal sleeping movement such as stretching out a leg.

Figure 6A:
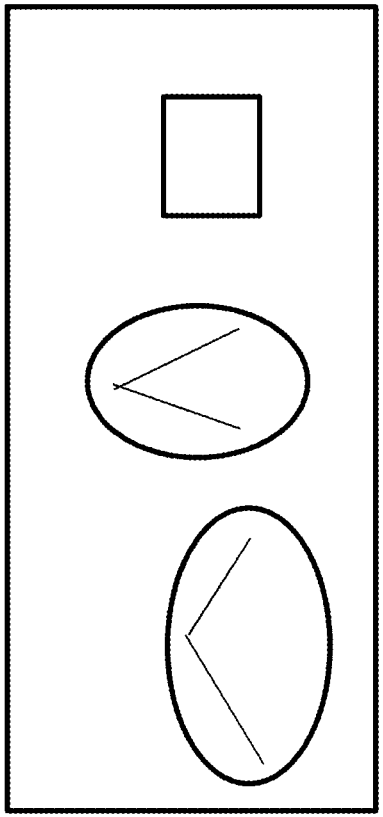
FIGS. 6A and 6B illustrate an exemplary annotated video image frame and a corresponding annotated difference image which include a covering over a subject and identify leg movement.

In FIG. 6A an exemplary video image frame of a patient supine on a bed is illustrated. The head is masked (black square) for patient confidentiality, a smaller circle annotates an area identified at the chest based on respiratory motion, and a larger circle annotates an area of motion identified as the legs. A sheet covers both the subject including the annotated areas. The image contrast shows a portion of the sheet in a tented position indicative of the legs in a bending or knees in a raised position.

Figure 6B:
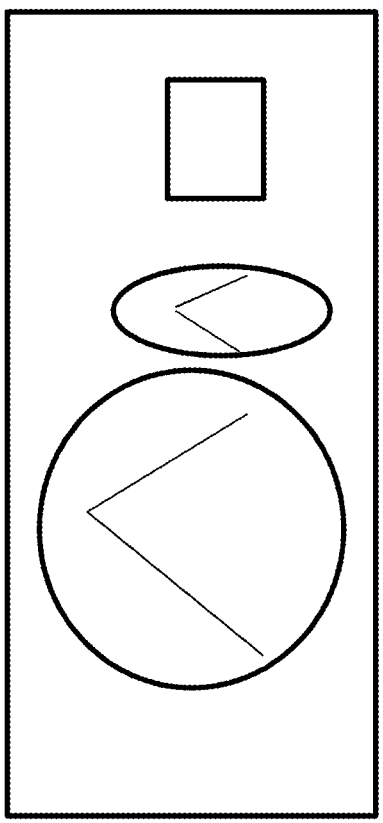

FIG. 6B annotates a difference image constructed from the image of FIG. 6A and a reference image. Three circles annotate the difference image corresponding to the circle annotations of the chest and legs in FIG. 6A and the head with no mask present. The motion cluster of the legs identifies the position of the legs which the segmentation unit segments. The cover spreads the motion cluster which is accommodated in the selected feature set to classify the motion. The orientation of the body axis can be observed from the orientation of the three annotated circles of FIG. 6B.

Figure 7A:
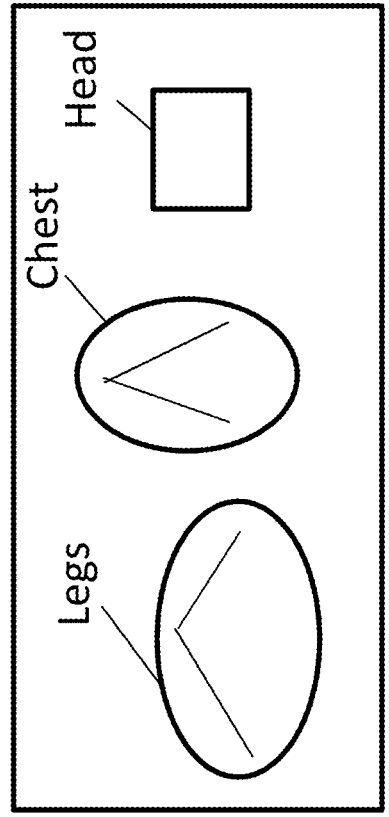
FIGS. 7A and 7B illustrate an exemplary annotated video image frame and a corresponding annotated difference image which include a covering over a subject and identify foot movement.

In FIG. 7A, an exemplary video image frame is shown just after the subject has lower bent legs of FIG. 6A. The right circle annotates the location of the segmented chest area. The left circle annotates the location of foot movement also covered.

Figure 7B:
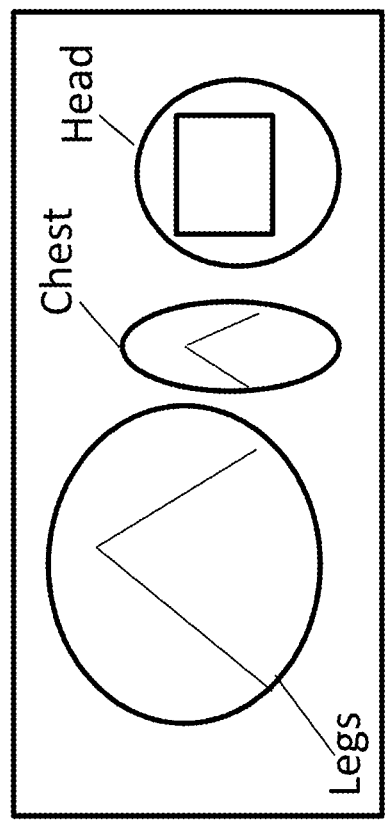

The three circles annotate the FIG. 7B difference image constructed from the image of FIG. 7A. The left most circle annotates the position of the motion cluster identified and segmented as feet. The center circle annotates the chest, and the right most circle annotates the head. The motion cluster between the chest and feet is not annotated, but shows the straightening of the legs.

Figure 8B:
FIGS. 8A and 8B illustrate an exemplary video image frame and a corresponding identified motion clusters which include leg, trunk, and head motion clusters and a fitted line of a subject body axis.
Figure 8A:
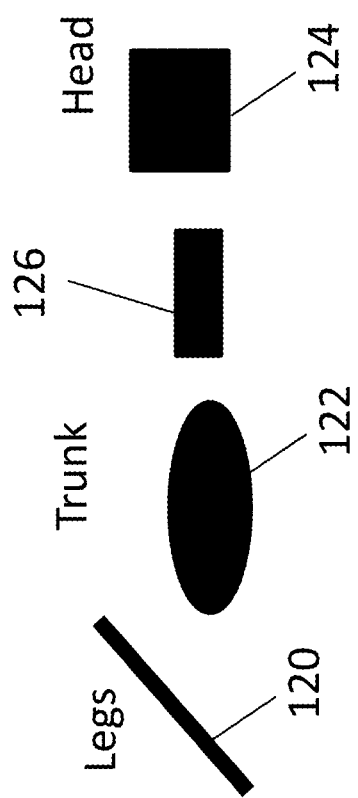

In FIG. 8A, a video image frame is shown with the subject on a bed without a cover. FIG. 8B shows corresponding motion clusters identified and segmented by body part and annotated as legs 120, trunk 122, and head 124. The uncovered cluster size is smaller and separation between clusters greater in comparison to the motion clusters in FIGS. 6B and 7B which include a cover. The body axis 126 orientation is illustrated by a line fitted to the clusters, e.g. least squares regression analysis.

Figure 9B:
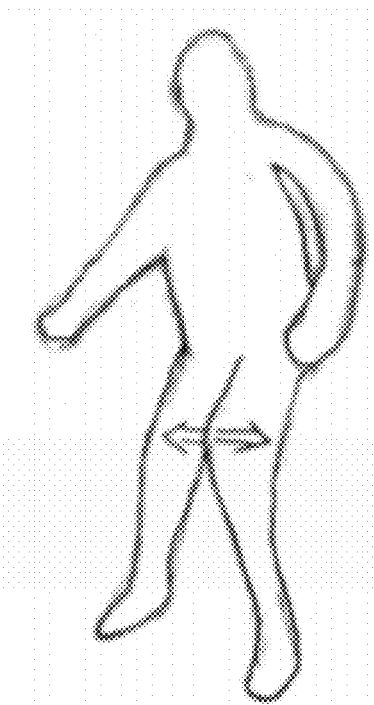
FIG. 9A and 9B illustrate an exemplary subject and motion vectors without and with a cover.
Figure 9A:
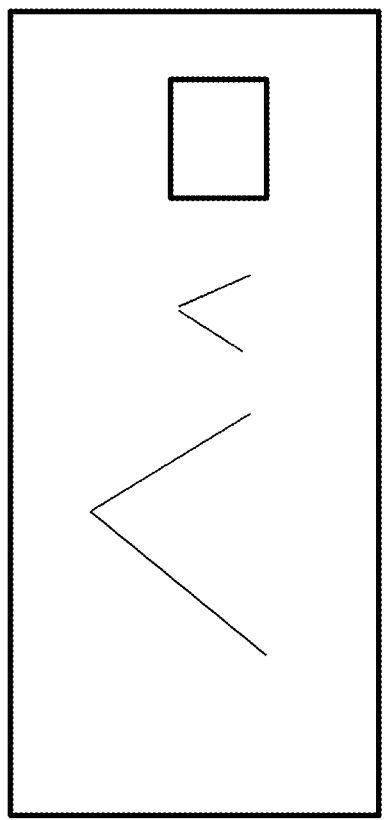

With reference to FIG. 9A, leg movement of a subject without a cover is illustrated. Motion vectors are indicated. The same leg movement is illustrated in FIG. 9B with the subject shown with a cover. The motion vectors are indicated which contrast with FIG. 9A for the same leg movement. Motion vectors with a cover are spread over the area of the cover, e.g., larger clusters in close proximity, and can include smaller, more multi-directional movement of the cover, e.g., close proximity between clusters representing shorter or different directional movement, as the cover moves with the underlying leg movement.

Figure 10:
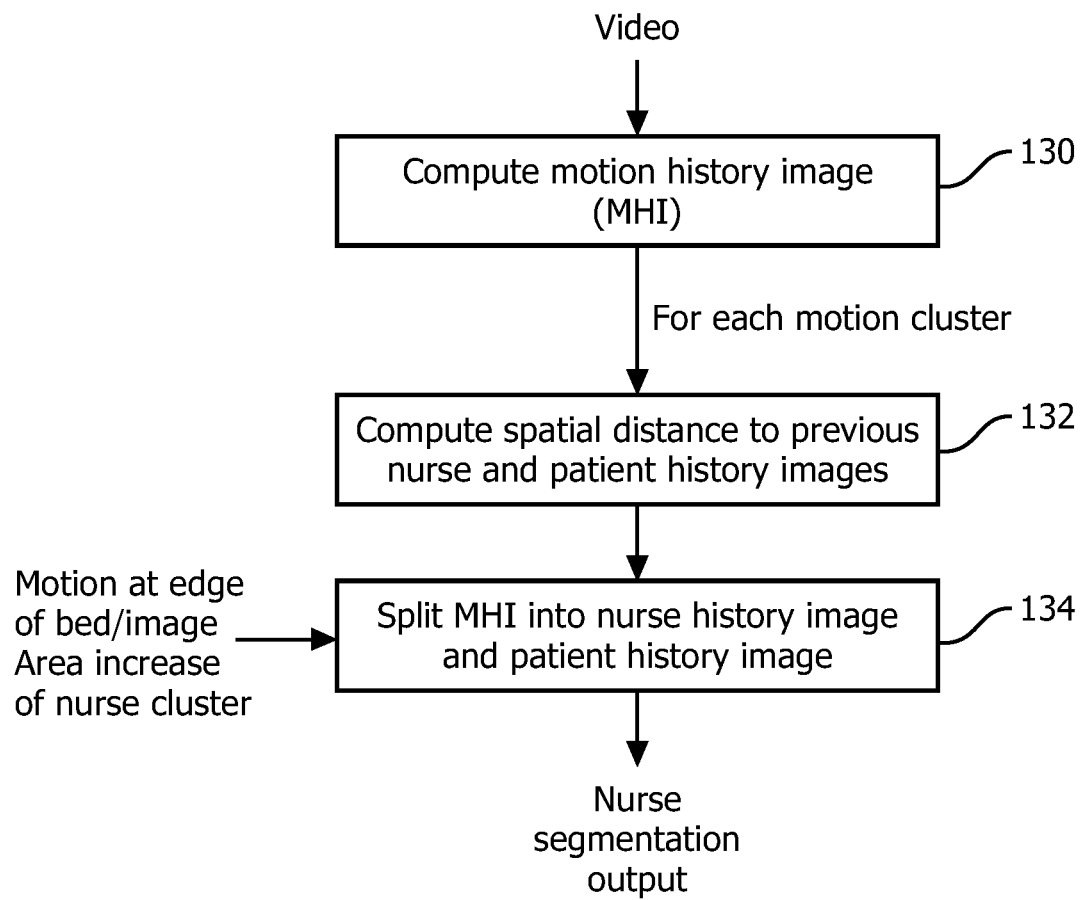
FIG. 10 flowcharts one embodiment of a method of movement analysis which includes separating motion of a third party.

With reference to FIG. 10, one embodiment of a method of movement analysis which includes separating motion of a third party is flowcharted. In a step 130, a difference image is computed and motion clusters identified. In a step 132, spatial differences to previous third party movement history and patient movement history are computed. Third party movement history such as healthcare practitioners or visitors is recorded in the third party data store 52. Subject movement history is recorded in the subject history data store 51.

Clusters are individually assigned to either a third party or the subject based on motion information at the edge of the bed or image, the motion cluster size increase, and spatial distance to previous third party movements and subject movements, e.g. historical images and/or recorded movements in a step 134. Motion at the edge of the image and/or bed and a small radius from subject movement history is assigned to the subject. For example, motions clusters where the patient is previously located in the center of the image and moves to the edge and no third party is previously detected are assigned to the patient. In another example, a motion cluster which extends from a previous patient movement cluster toward the edge, but no prior third party clusters are in temporal proximity or spatial distance, is assigned to the subject. Motion clusters in close spatial proximity to prior third party assigned clusters are assigned to the third party. A maximum amount of cluster increase, e.g. region growth is allowed for third party cluster motion detection. For example, the patient is located in the center of the image based on the current respiratory motion, and motion detected at the edge and does not exceed a maximum size is assigned to a third party. If the maximum amount of cluster increase is surpassed, the cluster is assigned to the subject, e.g. the patient has moved to the edge of the bed. Assigned clusters are record in the appropriate history.

It is to be appreciated that in connection with the particular illustrative embodiments presented herein certain structural and/or function features are described as being incorporated in defined elements and/or components. However, it is contemplated that these features may, to the same or similar benefit, also likewise be incorporated in other elements and/or components where appropriate. It is also to be appreciated that different aspects of the exemplary embodiments may be selectively employed as appropriate to achieve other alternate embodiments suited for desired applications, the other alternate embodiments thereby realizing the respective advantages of the aspects incorporated therein.

It is also to be appreciated that particular elements or components described herein may have their functionality suitably implemented via hardware, software, firmware or a combination thereof. Additionally, it is to be appreciated that certain elements described herein as incorporated together may under suitable circumstances be stand-alone elements or otherwise divided. Similarly, a plurality of particular functions described as being carried out by one particular element may be carried out by a plurality of distinct elements acting independently to carry out individual functions, or certain individual functions may be split-up and carried out by a plurality of distinct elements acting in concert. Alternately, some elements or components otherwise described and/or shown herein as distinct from one another may be physically or functionally combined where appropriate.

In short, the present specification has been set forth with reference to preferred embodiments. Obviously, modifications and alterations will occur to others upon reading and understanding the present specification. It is intended that the invention be construed as including all such modifications and alterations insofar as they come within the scope of the appended claims or the equivalents thereof. That is to say, it will be appreciated that various of the above-disclosed and other features and functions, or alternatives thereof, may be desirably combined into many other different systems or applications, and also that various presently unforeseen or unanticipated alternatives, modifications, variations or improvements therein may be subsequently made by those skilled in the art which are similarly intended to be encompassed by the following claims.

What is claimed is:

1. A monitoring system, comprising:
    at least one video camera configured to continuously stream a video of a subject in normal and darkened room conditions;
    a computer operatively connected with the at least one video camera, the computer programmed to:
    identify clusters of: (a) respiratory motion; and (h) body part motion of the subject in the video of the subject streamed by the at least one video camera;
    compute a difference signal based on comparison between a current, selected image and a plurality of reference images, the reference images being relative to the current image and from the streamed video of the subject,
    identify at least one additional cluster of respiratory motion in the streamed video of the subject based on the difference signal; and
    segment, on the streamed video, clusters of body part motion, and a head, chest, upper arm area or trunk portion of the subject[s ]based on the at least one additional cluster of respiratory motion of the subject in the streamed video.

2. The system according to claim 1, wherein the computer is further programmed to:
    identify a cluster of non-respiratory motion in the streamed video of the subject different from the identified clusters of respiratory and body part motion;
    generate a full body mask from the identified clusters of respiratory, non-respiratory, and body part motion;
    further segment, on the streamed video, clusters of body part motion, and the generated full body mask to generate at least one of a full body mask including body proportions or further segmented head, chest, upper arm area or trunk portions of the subject; and
    control a display to display the further segmented streamed video.

3. The system according to claim 2, wherein the computer is programmed to:
    compute attributes of the identified at least one additional cluster of respiratory motion and the identified duster of non-respiratory motion; and
    identify a presence and location or absence of a blanket covering the subject based on the computed attributes; and
    determine subject movement based on presence or absence of the blanket, at least one of the segmented head, chest, upper arm area or trunk portions of the subject in the streamed video, the identified at least one additional cluster of respiratory motion and the identified cluster of non-respiratory motion.

4. The system according to claim 1, wherein the computer is further programmed to:
    determine at least one measure of motion from the clusters of body part motion segmented on the streamed video; and
    classify motion based on the determined at least one measure of motion.

5. The system according to claim 1, wherein the computer is programmed to:
    determine a body axis orientation based on fitting a line through the clusters of body part[s] motion segmented on the streamed video, the body parts including a head and trunk.

6. The system according to claim 1, wherein the computer is further programmed to identify at least one cluster of motion in the streamed video of the subject associated with a third party different from the subject by:
    determining that at least one cluster of motion in the streamed video is greater than a predetermined distance from a previously identified at least one cluster that is associated with the subject.

7. The system according to claim 1, further including:
    a display device configured to display at least a portion of the streamed video of the subject.

8. A method of monitoring movement of a subject, comprising:
    with at least one video camera, continuously streaming a streamed video of the subject in normal and darkened room conditions;
    with at least one electronic processor, computing a difference signal based on comparisons between a current image and a plurality of reference images from the streamed video of the subject;

with the at least one electronic processor, identifying, in the streamed video at least one cluster of respiratory motion of the subject based on the difference signal; and with the at least one electronic processor, identifying in the streamed video, body parts of the subject based on the identified at least one cluster of respiratory motion of the subject, including segmenting an upper body of body parts based on the identified at least one cluster of respiratory motion of the subject.

9. The method according to claim 8, wherein segmenting the upper body includes identifying a head and a trunk based on body proportions and locations of the identified at least one cluster of respiratory motion of the subject.

10. A patient monitoring system, comprising:

a plurality of video cameras configured to continuously stream video of one subject which generates a streamed video of the subject; and at least one electronic processor operatively connected with the video cameras, the at least one electronic processor programmed to:

receive the streamed video;

compute a difference signal based on absolute differences between a current image and a plurality of reference images from the streamed video of the subject received from the video cameras, and identify a cluster of respiratory motion of the subject based on the difference signal;

segment an upper body of body parts based on the identified cluster of respiratory motion of the subject;

identify at least one cluster of non-respiratory motion in the streamed video of the subject;

segment at least a head and a trunk of the body parts based on the identified at least one cluster of non-respiratory motion and body proportions; and classify subject non-respiratory motion based on at least one measure of motion determined from the segmented at least a head and a trunk of the body parts.

11. The system according to claim 10, wherein the at least one electronic processor is further programmed to:

identify a presence and location or absence of a blanket covering the subject.

12. The system according to claim 10, wherein the at least one electronic processor is further programmed to:

determine a body orientation based on fitting a line through body parts segmented in the streamed video, the body parts including at least the head and the trunk of the subject.

13. The system according to claim 10, further including:

a display device configured to display at least a portion of the streamed video of the subject.

* * * * *